United States Patent
Hussam et al.

(10) Patent No.: US 10,311,036 B1
(45) Date of Patent: Jun. 4, 2019

(54) DATABASE MANAGEMENT FOR A LOGICAL REGISTRY

(71) Applicant: Universal Research Solutions, LLC, Columbia, MO (US)

(72) Inventors: Ali Adel Hussam, Columbia, MO (US); Andrea Wood, Columbia, MO (US)

(73) Assignee: Universal Research Solutions, LLC, Columbia, MO (US)

(*) Notice: Subject to any disclaimer, the term of this patent is extended or adjusted under 35 U.S.C. 154(b) by 176 days.

(21) Appl. No.: 15/204,818

(22) Filed: Jul. 7, 2016

Related U.S. Application Data

(60) Provisional application No. 62/265,205, filed on Dec. 9, 2015.

(51) Int. Cl.
  *G06F 16/22* (2019.01)
  *H04W 4/14* (2009.01)
  *G16H 10/60* (2018.01)
  *G06F 16/955* (2019.01)
  *G06F 16/2457* (2019.01)

(52) U.S. Cl.
  CPC ...... *G06F 16/2272* (2019.01); *G06F 16/2264* (2019.01); *G06F 16/2282* (2019.01); *G06F 16/24578* (2019.01); *G06F 16/9566* (2019.01); *G16H 10/60* (2018.01); *H04W 4/14* (2013.01)

(58) Field of Classification Search
  CPC ......... G06F 17/30336; G06F 17/30333; G06F 17/30339; G06F 17/30554; G06F 17/30864; G06F 17/30887; G06F 17/3053; G06F 17/30; G06F 19/322; G06F 16/2272; G06F 16/2282; G06F 16/9566; G06F 16/24578; G06F 16/2264; H04W 4/14; G16H 10/60; G06Q 50/24; G06Q 50/22
  See application file for complete search history.

(56) References Cited

U.S. PATENT DOCUMENTS

| | | | |
|---|---|---|---|
| 6,421,682 B1 | 7/2002 | Craig et al. | |
| 7,225,249 B1* | 5/2007 | Barry | G06F 17/3089 709/227 |
| 7,337,174 B1 | 2/2008 | Craig | |
| 2002/0035486 A1* | 3/2002 | Huyn | G06F 19/3418 705/3 |

(Continued)

FOREIGN PATENT DOCUMENTS

| WO | WO2015/077898 | 6/2015 |
|---|---|---|
| WO | WO2017/100609 | 6/2017 |

OTHER PUBLICATIONS

International Search Report and Written Opinion in corresponding Application No. PCT/US2016/065877, dated Apr. 20, 2017, pp. 1-7.

*Primary Examiner* — Anh Ly
(74) *Attorney, Agent, or Firm* — Fish & Richardson P.C.

(57) ABSTRACT

This document describes a data processing system for database management. The system includes a registry management server in communication with a logical registry in a data repository. The data repository includes profile data associated with profile objects, a library of electronic instruments and a logical table including a number of logical rows corresponding to the profile objects. The registry management receives profile data from a client device, selects electronic instruments from the library, and maps the electronic instruments and profile objects by updating the logical table and indexing the logical table.

25 Claims, 8 Drawing Sheets

(56) References Cited

U.S. PATENT DOCUMENTS

| | | | |
|---|---|---|---|
| 2003/0046113 A1* | 3/2003 | Johnson | G06Q 10/10 705/3 |
| 2005/0050173 A1* | 3/2005 | Kikuchi | G06F 17/30867 709/219 |
| 2005/0216312 A1* | 9/2005 | Bellin | G06Q 10/10 705/3 |
| 2007/0112724 A1* | 5/2007 | Beach | G06F 17/30286 707/E17.005 |
| 2008/0015916 A1* | 1/2008 | Cossey | G06Q 10/0637 705/7.36 |
| 2011/0071981 A1* | 3/2011 | Ghosh | G06F 11/2025 707/634 |
| 2013/0218596 A1* | 8/2013 | Gome | G06Q 10/06 705/3 |
| 2013/0291060 A1* | 10/2013 | Moore | G06F 21/6245 726/1 |
| 2013/0317753 A1* | 11/2013 | Kamen | G06F 19/3418 600/301 |
| 2014/0222443 A1* | 8/2014 | Danenberg | G01N 33/57407 705/2 |
| 2014/0245417 A1* | 8/2014 | Hu | H04L 63/0807 726/7 |
| 2014/0310261 A1 | 10/2014 | Nagpal et al. | |
| 2015/0025909 A1* | 1/2015 | Hayter, II | G06F 19/321 705/3 |
| 2015/0088805 A1* | 3/2015 | Kakarla | G06F 17/30306 707/600 |
| 2017/0091295 A1* | 3/2017 | Chandukutty | G06F 17/30297 707/E17.007 |

* cited by examiner

DATABASE MANAGEMENT FOR A LOGICAL REGISTRY

CLAIM OF PRIORITY

This application claims priority to 35 U.S.C. § 119(e) to provisional U.S. Patent Application No. 62/265,205 filed on Dec. 9, 2015, the entire contents of which are hereby incorporated by reference.

BACKGROUND

Data repositories are structured sets of data that can be accessed. Databases include the collection of schemas, tables, queries, reports, views and other objects. The data are organized to support processes requiring information.

A database management system (DBMS) is a system that interacts with a user, other systems, and the data repository to capture and analyze data. A general-purpose DBMS is designed to allow the definition, creation, querying, update, and administration of data repositories.

SUMMARY

This document describes a registry management server including one or more data processors and one or more storage devices in communication with the registry management server, the one or more storage devices configured to store a logical registry. The logical registry includes a data repository including first profile data associated with a profile object, the data repository being configured to receive the first profile data from the registry management server, a library of electronic instruments each associated with metadata for use in mapping the electronic instruments and the profile object by the registry management server, and a logical table including a number of logical rows intersecting a number of logical columns to define a number of logical cells, a logical row of the number of logical rows corresponding to the profile object. The registry management server includes one or more machine-readable hardware storage devices storing instructions that are executable by the one or more data processors to configured to perform operations including receiving second profile data from a client device, the second profile data associated with the profile object; selecting, based on the second profile data and the metadata, an electronic instrument from the library; and mapping the electronic instruments and the profile object by performing operations including updating the logical table by storing, in a logical cell of the number of logical cells, a reference to the selected electronic instrument, wherein the logical cell is in the logical row of the logical table corresponding to the profile object; and indexing the logical table.

In some examples, the operations can include generating electronic instrument data based on the selected electronic instrument; transmitting the electronic instrument data to a remote device; receiving, from remote device, response data associated with the electronic instrument data; updating the profile object with the response data; and responding to a query for data representing the profile object by returning the profile data, the response data, and the index of the logical row of the logical table corresponding to the profile object.

In some examples, selecting the electronic instrument from the library can include determining a subset of electronic instruments from the library of electronic instruments that are available for selection based on a procedure of the patient; for each electronic instrument of the subset: analyzing a score associated the electronic instrument, the score being based on one or more performance ratings for the electronic instrument; weighting the score based on a predetermined correlation between the electronic instrument and a value of an element of the profile object; identifying the electronic instrument for selection based on the weighted score for each electronic instrument.

In some examples, the element of the profile object can include one of patient demographics data, patient clinical data, patient recorded outcomes data, objective outcomes data, patient satisfaction data, patient education data, and patient billing data.

In some examples, the operations can include automatically enrolling the patient in a sub-registry of the logical registry, the sub-registry being related to the electronic instrument and being for a particular type of procedure data, wherein access to the sub-registry is limited to patients who have submitted to the sub-registry the particular type of procedure data.

Transmitting the electronic instrument data can include: selecting data representing a question of the electronic instrument for transmission to the remote device based on a characteristic of received data from a portable remote device; and generating an alert from selected data, with the alert including a universal resource locator (URL), which specifies a location of the registry management server for activating or viewing the selected data representing a question of the electronic instrument, wherein the alert activates a viewer application to cause the alert to display on the remote device and to enable connection via the URL to the registry management server over the Internet when the remote device is online.

In some examples, the operations can include transmitting an SMS message to the remote device requesting consent to receive the portable remote device data; receiving data representing the consent from the remote device; and requesting, from a third party server, the portable remote device data. In some examples, the operations can include generating a custom electronic instrument including the electronic instrument and additional questions based on the mapping between the electronic instrument and the profile object. In some examples, the operations can include generating a ranked list of a number of electronic instruments that are mapped to the profile object based on the profile data and the metadata; and transmitting, to the client device, data representing the ranked list.

All or part of the foregoing may be implemented as a computer program product including instructions that are stored on one or more non-transitory machine-readable storage media (or one or more machine-readable hardware storage devices), and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

BRIEF DESCRIPTION OF THE FIGURES

Like reference symbols in the various drawings indicate like elements.

DETAILED DESCRIPTION

Described herein is a data processing system for generating a logical registry, e.g., using information collected through various electronic instruments.

Figure 1A:
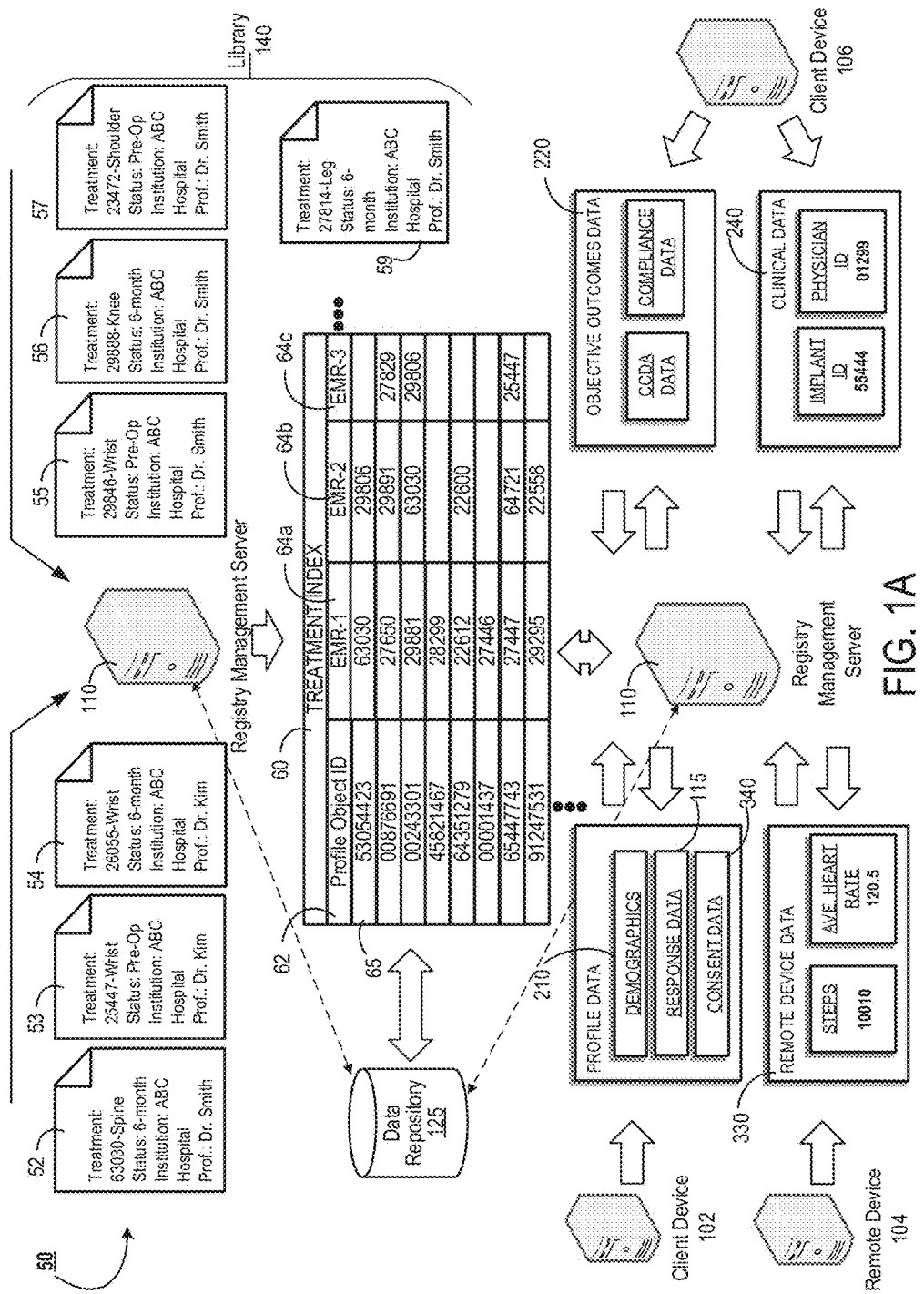
FIGS. 1A-1B are each diagrams of data processing systems that implement logical registries.

Referring to FIG. 1A, an example data processing system 50 includes a registry management server 110 in communication with a data repository 125. The registry management server 110 manages a database of the data repository 125. A library 140 is managed by the registry management server 110. The library 140 is includes one or more electronic instruments 112 (e.g., medical forms). The electronic instruments 112 can be validated or custom electronic instruments and are used to gather profile data 210 (e.g., patient data).

The electronic instruments 112 can include instruments for a number of procedures. In some examples, the electronic instruments 112 include standard electronic medical records (EMR) forms. For example, the electronic instruments 112 include a low-disk back surgery form 52, a repair wrist joints form 53, an incise finger tendon sheath form 54, a wrist arthroscopy/surgery form 55, a knee arthroscopy surgery form 56, a reconstruct shoulder joint form 57, a treatment of an ankle fracture form 59, and so forth. Each form can be associated with an identifier used to reference the form. In some examples, the identifier can be a standard EMR identifier. In some examples, the identifier can be a custom identifier.

The registry management server 110 is configured to communicate with other devices in the data processing system 50 such as the client devices 102, 104, the data repository 125, and the remote device 106. The data management server 110 receives data for populating a profile object 105 (e.g., a patient profile). For example, the data management server 110 receives response data 115, profile data 210, objective outcomes data 220, remote device data 330, clinical data 240, and other data for populating a profile object 105. The profile object 105 is associated with a particular patient. The registry management server 110 organizes the received data into the appropriate profile object 105.

When additional data is required for the profile object 105, an electronic instrument 112 can be used to collect the data from the client devices 102, 106, and the remote device 104. In some examples, additional data is required for compliance with a registry standard. The registry management server 110 can communicate with the data repository 125 to access the library 140 and retrieve an electronic instrument 112. The library 140 is indexed for quick retrieval of an electronic instrument 112 by the registry management server 110. When an electronic instrument is needed, the registry management server 110 can generate an instance of the electronic instrument object of interest for transmitting to a client device 102, 106 or remote device 104. A user can populate the electronic instrument 112 with data (e.g., profile data 210, objective outcomes data 220, clinical data 240, etc.) from a device such as a client device 102 of the patient, a client device 106 of a medical entity, or a remote device 104. For example, profile data 210 can be needed for a registry. The registry management server 110 selects and requests an electronic instrument 112 from the library 140. The electronic instrument 112 is transmitted to the appropriate client device 102, 106. The client device can return data depending on the type of electronic instrument 112. For example, client device 102 associated with a patient can return response data 115, consent data 340, demographics data 210, and so forth. For example, client device 106 can return objective outcomes data 220 (e.g., CCDA data, compliance data, etc.), clinical data 240 (e.g., implant identification, physician identification, etc.), and so forth. The registry management server 110 aggregates the received data into the appropriate profile object 105 in the data repository.

To select an electronic form 112 for transmitting to a client device 102, 106, the registry management server 110 uses a logical table 60. The logical table 60 is built using data in the profile object 105 and maps one or more electronic instruments 112 to a profile object 105. Predetermined correlations between the data in the profile object 105 and the electronic instruments 112 to determine which electronic instruments 112 are needed for a profile object 105. The process for selecting an electronic instrument 112 is described in further detail in relation to FIG. 6.

The logical table has logical rows, columns, and cells. Each logical row 65 includes a profile object reference 62. The profile object reference 62 can be an identifier and the reference associates the referenced profile object with the logical row 65. A number of logical columns 64a, 64b, 64c, and so forth can be used to generate logical cells for holding data representing references to electronic instruments 112. Each logical row 65 includes the profile object reference 105 for that row and any electronic instruments 112 that have been mapped to that profile object 105. The electronic instruments 112 can be referenced using metadata, such as an EMR identifier. The logical table 60 is stored in the data repository 125 and is indexed so that the data management server 110 can access the mapped electronic instruments 112 with low latencies. By generating electronic instruments 112 as needed, the data processing system 50 can save storage space in the repository 125. By selecting the appropriate electronic instrument 112 based on profile data, the data processing system 50 can customize registries to include data that are more meaningful and more tailored to the needs of a registry owner or user.

Figure 1B:
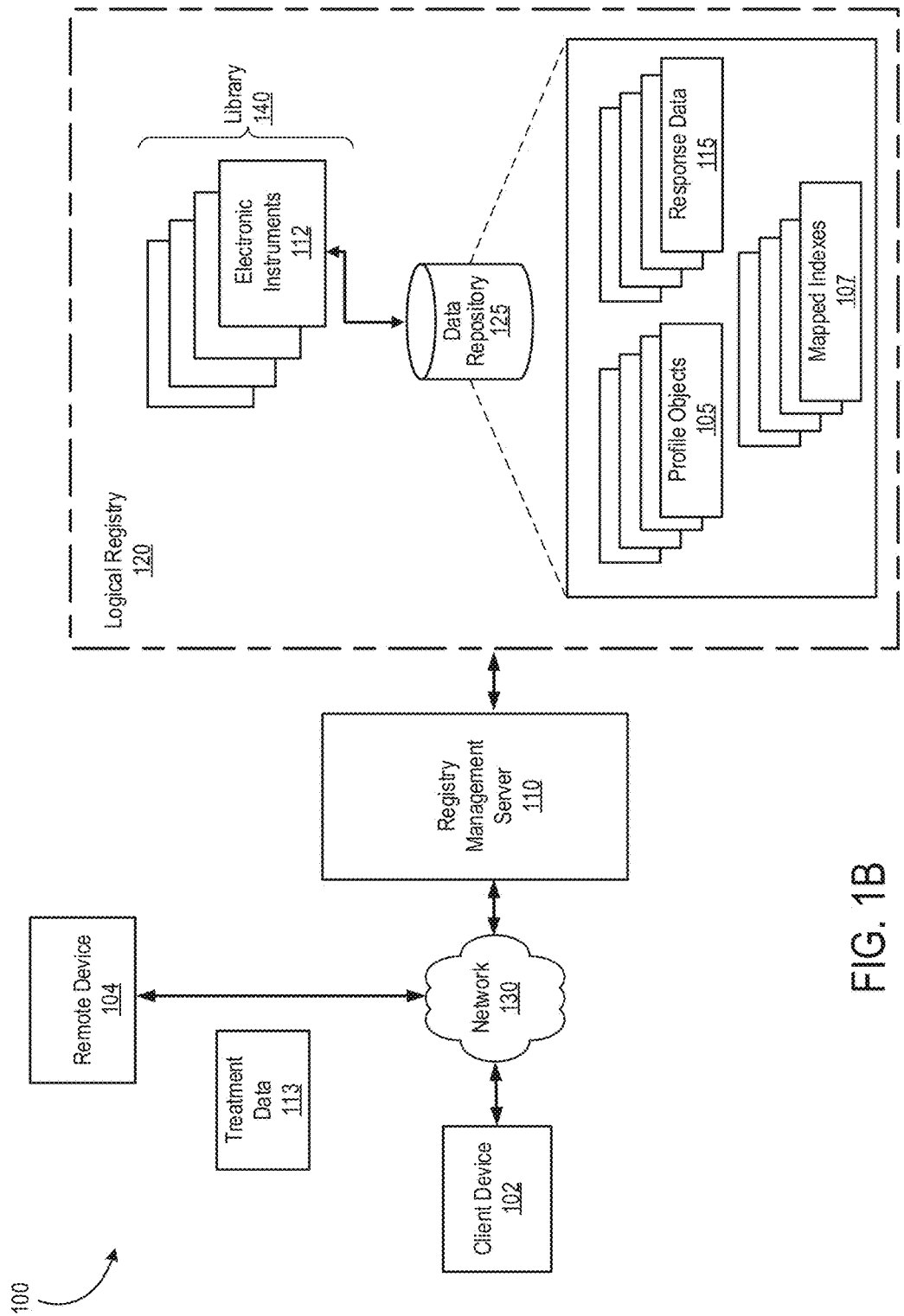

Referring to FIG. 1B, the data processing system 100 includes a registry management server 110 and a logical registry 120 (e.g., a medical registry). The registry management server 110 can communicate with a remote device 104 and a client device using a network. The logical registry 120 includes a library 140 of electronic instruments 112 (e.g., electronic instruments) and a data repository 125. The library is indexed for quick retrieval of electronic instruments by the registry management server 110. The data repository 125 includes profile objects 105 (e.g., patient profile objects) and response data 115 (e.g., patient response data 115). A separate hospital logical registry 120 can be associated with the client device and can communicate with the registry management server 110 using the client device and the network 130.

Generally, a logical registry 120 includes a repository (e.g., data repository 125) for procedure/treatment data and data that is made available and/or viewable. To facilitate searching of the logical registry 120, data are often input into the logical registry 120 in a specified format, e.g., according to data specifications. For example, a database may require that a search query or search term have a specified number of letters and/or numerals and/or have a pre-fix.

To facilitate searching, a logical registry 120 is segmented into various areas, e.g. registries, to allow a user to search a specific area. For example, the various areas may be based on data categories (e.g., medical specialties and/or areas of medicine). There may be a cardiology area (e.g., for storage of cardiology information), an implants area (e.g., for storage of information indicative of medical implants), an outcomes area (e.g., for storage of information indicative of medical outcomes of various medical procedures and treatments), and so forth.

The logical registry 120 includes a library 140 of electronic instruments 112. The electronic instruments 112 are related to one or more procedures (e.g., medical treatments). In this example, electronic instruments 112 include various types of electronic instruments 112 with questions for collecting information. In an example, the electronic instrument 112 is specific to a particular service provider and is accessible to patients of that service provider. In another example, the electronic instrument 112 is accessible to patients who satisfy pre-specified criteria, e.g., such as possessing a particular medical problem. In an example, the electronic instruments 112 are pre-validated or pre-approved by one or more users of the logical registry 120, such as research or regulatory bodies, as including the information necessary to be of use to one or more outcomes studies, research studies, or other uses of the logical registry 120. The electronic instruments 112 are each associated with metadata that can be used to identify, sort, rank, reference, select, or otherwise manipulate the electronic instruments 112 in the library 140. In some examples, the metadata includes a standardized identifier, such as an Electronic Medical Record (EMR) code. In some examples, the metadata includes a benchmark score, a date of entry, a ranking, compliance data, completeness data, and so forth.

The data repository 125 includes profile objects 105, response data 115, and mapped indexes 107 data. The profile objects 105 include profile data related to one or more procedures of the patient. Profile objects 105 can include demographics data 210, patient clinical data, outcomes data (e.g., patient recorded outcomes (PROs) data), objective outcomes data 240, patient satisfaction data 250, patient education data 260, patient billing data 270, and references to indexes mapped electronic instruments 112. For example, if a patient had spinal surgery, the profile data can include the date of the operation, pre-operation patient feedback regarding quality of life, pain levels, etc., physician information, and post-operation outcomes information. The profile objects 105 are described in detail in relation to FIG. 2.

Profile data associated with treatment of the patient is collected for updating the profile object 105 in a number of ways. In one example, the electronic instrument 112 can be used to collect profile data for including in the profile object 105. The registry management server 110 sends the electronic instrument 112 to the client device 102 or remote device 104. In response, the client device 102 or the remote device 104 sends treatment data 113 (via an automated and automatic data feed that is preconfigured to interface between the registry management server 110 and remote device 104 and/or client device 102) to the registry management server 110. In this example, treatment data 113 includes treatment data that is received from one or more entities (e.g., medical offices, electronic medical record (EMR) systems, hospitals, and so forth). In this example, treatment data 113 includes answers to questions included in the electronic instrument. The registry management server 110 parses and analyzes treatment data 113 and stores/updates logical registry 120 with the treatment data 113 (e.g., after formatting treatment data 113 as needed). In an example, a logical registry 120 is updated by inserting information into a database record to transform the database record.

In some examples, the profile data is collected from a remote device 104. The remote device 104 can be a portable device. The portable device can be used to collect data for the networked system. The portable device can include a computer processor, one or more sensors which can gather data, and a means for transmitting data using one or more of the wireless devices and the network 130. In some examples, the portable device can store portable device data using a means for storing data such as solid-state storage, a hard drive disk, or other storage device, for later transmission. The patient can be portable such that a patient can carry the portable device. In some examples, the remote device 104 can be a mobile communication device, such as a smartphone. In some examples, the remote device 104 can be worn by the patient. Some examples of a wearable device include Fitbit produced by Fitbit of San Francisco, Calif.; smartwatches such as the Apple Watch produced by Apple of Cupertino, Calif.; and similar devices. The remote device 104 can be a laptop, tablet, desktop computer, or other computing device.

In some examples, the remote device 104 that is portable is used to monitor activity, such as physical activity, of the patient and gather portable device data relating to the activity of the patient. The profile data collected by the portable device can include one of the type of measurement of patient activity, such as a number of steps taken by the patient; a distance the patient has run walked, jogged, or the like; a heartrate of the patient; approximate calories burned by the patient; sleep patterns of the patient; a number of stairs climbed by the patient; or other data representing activity by the patient. The profile data collected by the remote device 104 includes an identifier relating the measurements of patient activity to a particular patient. The identifier can be used for associating the portable device data with the proper profile object 105 in the data repository 125. In some examples, the portable device can transmit data wirelessly using the wireless device and the network 130. In some examples, more than remote device 104 can be used to monitor activity and gather profile data. In some examples, the remote device 104 can be the client device 102.

The data collected by the remote device 104 is formatted and added to the profile object 105 and can be used by the registry management server 110 for several purposes. The collected data can be used for mapping an electronic instrument to the profile object 105 or creating a custom electronic instrument for the patient. In some examples, the collected data can be used to trigger alerts or reminders that are sent to the remote device 104 or the client device 102 reminding a user that the electronic instrument 112 should be completed, transmitted or other action needs to be taken in relation to the an electronic instrument 112 or registry associated with the profile object 105.

In some examples, data is collected from the remote device 104 after an alert is sent to the remote device 104. The alert can include information such as a message, instruction, question, notification, form, or other such information. The alert can be transmitted in the format of an SMS message, IVR message, email, push notification, or a similar format. In some examples, alert includes an alert having a universal resource locator (URL) specifying a location of a system for activating or viewing the selected alert. The conditions in which the registry management server 110 selects and transmits alert to the client device 102 related to a particular patient can be designated. Once alert has been selected by the registry management server 110, the alert can be transmitted to the client device 102 based on the destination address of the client device 102.

The remote device 104 can be used to receive the alert from the registry management server 110. The remote device 104 can include a computer processor, a means for receiving alert, a user interface, and a means for transmitting response data 115 using the network 130. The remote device 104 can be a computer, mobile phone, tablet, laptop, or other such device. The remote device 104 can be a wireless device, which can connect to the Internet. In some examples, the remote device 104 can be the same as the portable device or the client device 102. In some examples, the alert can be received by more than one remote device 104. The alert can appear on the user interface as an instruction (e.g., such as a selectable link or hyperlink, also referred to herein as hyperlink) in the form of a message, notification, question, or other such instruction. In some examples, the alert appears as a URL link specifying a location of a system for activating or viewing a prompt screen that displays one or more questions from a validated electronic instrument 112, custom electronic instrument 112, a stand-alone question, or other query for the patient based on the need of the profile object 105. As described herein, electronic instruments 112 include outcomes form for collection of outcomes data. In this example, upon selection of the hyperlink, remote device 104 sends a request to registry management server 110 for one or more outcomes questions. In response to the request, registry management server 110 selects an appropriate question from an appropriate one of electronic instruments 112 and sends to remote device 104 data (which may also be referred to as prompt data, as it prompts the user to input data) representing the selected question for rendering in graphical user interface.

A trigger module is used to designate the trigger used for determining whether to select and transmit the alert to the remote device 104 using the network 130. The trigger can be a threshold, differential, range of values, or trigger condition that can be met by collected data.

The action module is used to designate what action the patient should take upon receiving the alert or notification. As previously described, the alert can require the patient to select a URL sent to the remote device 104 that specifies a location of a system for activating or viewing the action. In some examples, data indicative of the action specified is rendered on the client device 102 independent of link selection). Once the link or notification has been activated, the action can require the patient to answer a question, fill out a form, rate pain, or otherwise submit response data 115 to the data processing system. The action can activate an application on the remote device 104 that causes the user interface to display a question, form, or other action for the client to use to submit response data 115. Other methods and systems for collecting profile data can be found in application Ser. No. 14/991,379, which is incorporated herein in its entirety.

The network 130 can be used to transmit data from one device to another in the registry management server 110. The network 130 can include wired communications links and wireless communications links. The communications links can use network protocols such as TCP/IP, Bluetooth®, Ethernet, or other network protocols. The communications links can use communication protocols such as HTTP, IMAP, POP, or other communication protocols. In some examples, the communications links can use one or more of SMS and IVR messaging communication standards.

The network 130 can include a wireless device. The wireless device includes one of Wi-Fi routers, Wi-Fi access points, and wireless tracking devices, beacons, computing devices, laptops and so forth. In some examples, wireless device include cellular networks such as LTE networks. The wireless device can communicate via the network 130 to the registry management server 110 and communicate with the client device 102 and the remote device 104. In some examples, the wireless device can communicate via the network 130 to the hospital logical registry 120. In some examples, wireless device is a fixed-location wireless device, such as a fixed-location router or computer. In other examples, the wireless device is discoverable (e.g., by the registry management server 110), when the wireless device is connected to a network or connected to a port.

In an example, the logical registry 120 has one or more sub-registries having different levels of flexibility. Because not every sub-registry has the same needs and goals, the system provides different models of sub-registries, each with varying levels of required data, setups, and features. The data processing system is also configured for automation of data procurement and feeding to the logical registry 120, as the logical registry 120 is designed to be as minimally invasive as possible to a physician's current workflow. As such, once a physician's office or hospital joins the logical registry 120, the system automatically releases electronic instruments 112 to patients, sends reminders to patients, and feeds this data to the logical registry 120. Various types of registries and sub-registries are described below.

The logical registry 120 or a sub-registry requires the setting of standards for submission of implants data, outcomes data, and demographics data 210, and so forth. Additionally, the system is accessible to registered and/or licensed users of the system (e.g., the registry management server 110). In some examples, logical registry 120 data is available to all users (e.g., in de-identified form).

In an example, the data processing system is configured for integration with the individual or group's practice management system for full automation of profile data filling into the system (e.g., when the individual or group has a license for the system). The system is configured for full automation of electronic instruments 112 being sent to the patient participants and auto feeding to the registry database. In another example, the system is configured for automation of forms to patient participants and auto feeding to the registry database (e.g., via a Lite license). This option is independent of an interface between the system and a practice management system, which requires manual entry of patient participants into the system.

The electronic instruments 112 include instruments for collecting outcomes data. Standards for outcomes data, implants, and other data points are set by the registry administrators and are required for submissions. Throughout the data collection process, participants are granted real-time access to the de-identified database (e.g., a logical registry 120 in which patient identifying information such as a name, age, address, social security number and so forth is removed). Participants also have access to the system's data mining module, which includes statistical functions, graphing, and export to CSV, and access to a raw export tool. In an example, the system includes a predictive modeling component that uses statistical methods to predict, or forecast trends to identify patients that are at risk based on the outcomes data and other collected data points.

The data repository 125 includes response data 115. The response data 115 includes outcomes data and scores includes outcomes data provided by or on behalf of the patient. Outcomes data includes, for example, results of a procedure and information related to therapy or treatment undergone by the patient. The outcomes data can be provided to the data repository 125 in the form of response data 115 provided by the remote device 104. The outcomes data can be entered into the profile object 105 by updating one or more entries in the profile object 105 data with the received outcomes data. In some examples, the patient may complete a standardized form by answering questions and rating his or her condition, such as pain experienced or other metrics, in a standardized format. The rating can be in the form of a numerical score. The outcomes data can be accessed by a physician or other medical entity to monitor the progress, compliance, and efficacy of the therapy of the patient or a group of patients. The outcomes data can be associated with one or more of demographics data 210, satisfaction data 250, procedure data, implant data, or other data of the profile object 105. The outcomes data can be used to determine an assessment of care for the patient, such as changing a prescribed therapy regime to increase efficacy, reduce injury, or other goals. The outcomes data can be gathered by the use of electronic instruments 112.

For collecting profile data, in one example, the registry management server 110 establishes a connection (e.g., a virtual private network connection) with a client device 102 (that implements an institution/group practice management system) and is used to pass scheduling (SIU) and patient demographics (ADT) messages from the institution/group practice management system to the registry management server 110. The registry management server 110 automates the collection of outcomes data on preset timelines. Physicians can scan or key in implants data directly into the registry management server 110. In this example, the registry management server 110 will work with the implants company to create a pre-populated list of implants that is included in within an operative form. All collected information is auto fed to the registry database. Registry data can be accessed in real-time through the Oberd data-mining module or through a full export of the data.

In another example, submission of information is independent of an interface existing between the registry management server 110 and the institution/group practice management system. In this example, patient demographic and surgery dates are manually entered into the system. Following the manual entry of patient demographics, the full automation of the system is available, including, e.g., the reporting and data retrieval. Electronic instruments 112 are sent at preset time intervals. Implants data input is automated through the preset list of implants. Data is auto fed to the registry database, with real-time access to data-mining module and the export tool.

In another example, not all electronic instruments 112 or questionnaires for outcomes data are in the library 140 of the data repository 125. For new validated electronic instruments 112 requests, the system will follow the following protocol. The system determines if any licensing or copyright requirements exist to use the electronic instrument 112. If there are no copyright/licensing requirements, the system will input the electronic instrument 112 exactly as displayed in the provided copy or the most official version. The system will apply a scoring algorithm to results of the electronic instrument 112, e.g., to assess the effectiveness of certain procedures and/or devices. If there are copyright/licensing requirements, the system contacts the authors of the validated electronic instrument 112 to determine the requirements of the copyright/licensing. If there are costs assessed for the use of the validated electronic instrument 112 within the system, the system will determine internally if that cost will be passed to the users of the registry.

The most commonly used electronic instruments 112 assess one of the following attributes: symptoms (impairments) and other aspects of well-being, functioning (disability), health status, general health perceptions, health related quality of life (HRQoL) and reports and Ratings of health care. Measures of symptoms may focus on a range of impairments or on a specific impairment such as depression or pain. Measures of functioning assess activities such as personal care, activities of daily living and locomotor activities. Health-related quality of life instruments are generally multi-dimensional questionnaires assessing a combination of aspects of impairments and/or disability and reflect a patient's health status. In contrast, QoL goes beyond impairment and disability by asking about the patient's ability to fulfill their needs and about their emotional response to their restrictions. In an example, a patient is prompted to rate (e.g., select a value for) each attribute in the electronic instrument 112. The registry management server 110 then scores the electronic instrument 112 by aggregating the selected value. This provides a score for an outcome of a particular procedure and/or an outcome of a particular medical device.

The registry management server 110 also implements a questionnaire timeline. The system determines the time points at with the outcomes data should be collected prior to and following their surgery. For example, the registry may determine to collect outcomes data at the follow time points: pre-op, 6 weeks, 3 months, 6 months, 1 year, 2 years, 3 years, 4 years, and 5 years. The time points will be locked for the logical registry 120 and all patients included in the logical registry 120 will receive a request for outcomes data at those time points.

The system allows for customization of the amount of time in which a patient has to fill her electronic instrument 112 at each time point. For example, the patient may be given the full length of time between the scheduling of their surgery and until the day of surgery to fill their electronic instruments 112 for the "pre-op" time point. For the 6-week time point, the patient could be given 2 weeks to complete the assigned electronic instruments 112.

The registry management server 110 also includes a data-mining module. The data mining module offers real-time access to data submitted to the registry with statistical functions and the ability to export filtered data to a CSV file (typically used within excel, SPSS, or SAS). The data mining module supports filtering by physician (if enabled in the registry permissions), PRO, patient demographics (age, gender, BMI, comorbidities, ICD—☐9 code, or CPT code). Trends are shown through a graph. Patient privacy is incorporated into the graphs, e.g., as physicians can see protected health information (PHI) identifiers for their own patients only. All data mined from the registry database is de-identified. In an example, the graph includes an outcomes data score, and time interval at which the form was filled (in relation to the surgical encounter). In this example, the standard deviation automatically is calculated and displayed. The mean and correlation is automatically calculated.

Additionally, trends are also shown through a table, in which the registry management server 110 ensures patient privacy by enabling physicians to see PHI identifiers for their own patients only. Data mined from the registry database is de-identified. In some example, the table displays patient name, outcomes data score at each time interval (in relation to the surgical encounter), surgery date, gender, age, physician, and institution/group. Through the data-mining module, users have the ability to see individual responses to electronic instrument 112 questions. The registry management server 110 also supports keyword searching and exporting to a data file.

The trends can show how elements of the profile object 105 are interrelated. For example, if a particular patient demographic correlates strongly with a particular outcome, future enrollment of patients in a registry or mapping of an electronic instrument 112 to a patient can be changed to get results that are more meaningful from the electronic instruments 112. In one example, if a patient having a particular occupation is affected in a particularly adverse way by an operation, the patient might rate her quality of life to be low despite a successful operation. For example, if a professional pianist undergoes hand surgery, the quality of life score for the pianist might be low despite a successful surgery as compared to the same operation and result on a professional sprinter. In another example, a middle-income patient might rate his quality of life to be poor after an expensive but successful procedure, while a wealthy patient might report a high quality of life after the same procedure with the same physical outcome.

The correlations between different elements of the profile object 105 can be used by the registry management server 110 to map one or more electronic instruments 112 to profile objects 105, as described below. Electronic instruments 112 can have metadata identifying significant correlation with one or more elements of profile objects 105 to help weight the electronic instrument 112 for mapping to profile objects 105. This metadata gives the electronic instruments 112 context for use and allows a greater granularity in the mapping of an electronic instrument 112 to a profile object 105.

The registry management server 110 also includes a predictive module that uses statistical methods to predict, or forecast, which patients are the greatest risks for a certain outcome, such as readmission, based on data collected.

The scores for the electronic instruments 112, such as the outcomes data scores, electronic instruments 112 statistics, trends, and other data collected using the data-mining module are used for mapping other electronic instruments 112 to profile objects 105. For mapping the electronic instruments 112 to one or more profile objects 105, the correlations determined by the data-mining module, trends, prediction module, or other analysis modules. Eligible electronic instruments 112 are first determined from the library 140. For example, if a patient is in a particular sub-registry but not others, certain electronic instruments 112 from the library 140 can be excluded as irrelevant. Once a subset of electronic instruments 112 has been determined, the registries management server can analyze scores of the electronic instruments 112. The scores of the electronic instruments 112 are based on ratings of the electronic instruments 112 given by registry operators, physicians, researchers, or other users of the logical registry 120. In some examples, the scores reflect how useful an electronic instrument 112 has been over time in producing data for profile objects 105. For example, if an electronic instrument 112 is hard to understand, badly phrased, off-topic, too long, etc. the electronic instrument 112 can have a poor rating. The score of the electronic instrument 112 is then weighted based on the identified correlations to one or more elements of the profile object 105 for which the electronic instrument 112 is a potential match. If the correlations are strong, the weight might positively bias the electronic instrument 112 to be mapped to the particular profile object 105.

The weighted score of an electronic instrument 112 is used to map the form to the profile object 105. In some examples, all electronic instruments 112 above a score threshold are mapped to the profile object 105. In some examples, the highest scoring electronic instrument 112 is mapped to the profile object 105. In some examples, electronic instruments 112 above a threshold are presented to the user of the logical registry 120 in a visual representation as a ranked list. The ranked list can show the raw scores and the weighted scores of each electronic instrument 112 mapped to a profile object 105 so a user, such as a researcher or physician, can make the final selection of which forms to map to which patients. In some examples, the patient can be enrolled automatically in registries for the mapped electronic instruments 112 or can be automatically assigned a form timeline based on the mapping.

The mapping of an association between the profile object 105 and the electronic instrument 112 is a reference that is in the profile object 105 data. This reference can be a pointer, link, identifier, or other data that associates the electronic instrument 112 data to the profile object 105 data. When an electronic instrument 112 is sent to a patient to be completed, the electronic instrument 112 can be generated in real-time or near real time and transmitted to the remote device 104 or client device 102. This configuration reduces the storage space necessary to relate electronic instruments 112 to profile data and grants the registry management server 110 greater flexibility in handling the library 140, the electronic instruments 112 and their metadata, the profile objects 105, and the response data 115. In this example, no copies of electronic instruments 112 need be stored in the profile objects 105, reducing storage requirements. The profile object 105 can be mapped to several electronic instruments 112 in various registries without requiring special permissions to access registries or sub-registries of which the patient is not a member allowing cross-pollination of logical registries' correlation data and without tainting a study by adding unnecessary patients to the registry. An example of the mapping is described in detail in relation to FIG. 4.

The registry management server 110 is also configured for automation of enrollment in one or more registries based on the electronic instruments 112 that are mapped to the profile object 105. In this example, the registry management server 110 implements a release of forms. Electronic instruments 112 such as patient-reported outcomes will be automatically assigned and sent electronically to patients according to the release timeline created during the logical registry 120 or sub-registry setup. The release timeline is set according to a "surgical date" and then uses the surgery date of each patient to assign the electronic instruments 112 accurately. System also implements patient reminders. As electronic instruments 112 are assigned and available for a patient to fill, based on the registry release timeline, patients will receive an email from the registry management server 110 reminding the patient. The email will indicate patient's agreement to participate in the study, instructions on how to access the forms, a link to a patient portal of the registry management server 110.

In this example, the registry management server 110 implements a patient portal for accessing and viewing patient form. The patient can access the patient portal through the secure link provided in the email reminder or through a link that the institution provides upon scheduling the surgery or includes on their website. If the patient accesses the patient portal through the secure email link included in the reminder, they will only be required to provide one level of authentication. By default, this level of authentication is a security answer set by the patient on their initial login. Accessing the patient portal through an institution link (and not through an email invitation) will require the patient to provide two levels of authentication, e.g., patient name, date of birth, last four digits of social security number or patient identifier, security answers, which are set by the patient upon initial login, and so forth. Within the portal, the patient can complete all pending questionnaires and review any questionnaires they have previously completed. As previously described, the registry management server 110 is configured to capture implant data, e.g., via a barcode scan and/or via manual entry.

Figure 2:
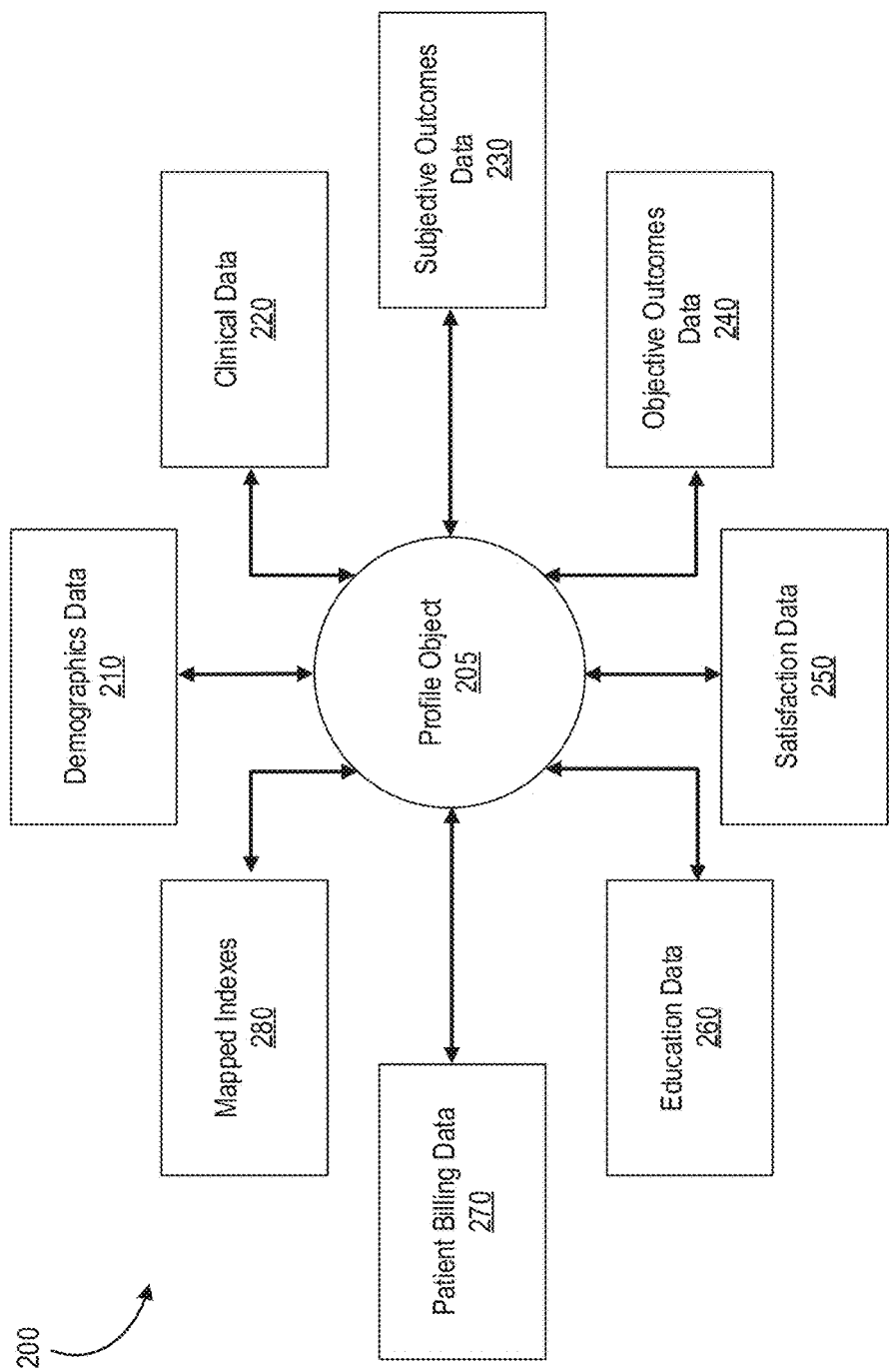
FIG. 2 is a diagram of an example profile object.

FIG. 2 shows an example diagram 200 of a profile object 205. The profile object 205 includes one or more of patient demographics data 210, patient clinical data 220, subjective outcomes data 230, objective outcomes data 240, patient satisfaction data 250, patient education data 260, and patient billing data 270. The profile object 105 can also include mapped indexes 280 referencing mapped electronic instruments 112 associated with the profile object 105.

Demographics data 210 is included in the profile object 105. For example, demographics data 210 can include one of age, gender, race, weight, height, and the like. One type of demographic data is comorbidities data and information indicative of Complex Chronic Disease (CCD). In this example, a client device 102 sends an electronic medical record (EMR) to the registry management server 110 and the registry management server 110 can parse the EMR for a CCD to include in the logical registry 120 or include the electronic instrument 112 in the library 140. Additionally, the data processing system uses an electronic instrument 112 to collect desired demographic data, if the requirements exceed age, gender, race, and ethnicity.

The profile object 105 includes clinical data. Clinical data includes a patient history, physical exam information, op-notes, and Electronic Medical Records (EMR) data. In some examples, EMR clinical data include the Consolidated Clinical Document Architecture (CCDA) data. The CCDA data is clinical data in a standardized format suitable for a Health Information Exchange (HIE). In some examples, the CCDA data can be accessed from a CCDA system using an application program interface (API) associated with the CCDA system. In some examples, CCDA system is a server associated with a medical entity.

The CCDA data conforms to the CCDA and can include CCDA documents. The CCDA can standardize the content and structure for clinical care summaries by using pre-defined attributes. CCDA documents are coded in XML and XHTML. CCDA documents can include a header that enables exchange of clinical documents within and across institutions. CCDA documents include a patient identifier. CCDA documents can include a body that includes the clinical report and one or more sections, such as allergies of a patient, medicine used, vital signs, immunizations, and the like. The body can include a narrative block. The body can include machine-readable entries. The registries management server can use one or more CCDA patient identifiers to identify a number of patients associated with an attribute of interest in the CCDA documents.

The profile object 105 includes outcomes data (e.g., patient-recorded outcomes data). Outcomes data can include subjective outcomes data 230. Outcomes data can be collected using a questionnaire for a clinical trial or in a clinical setting, where the responses are collected directly from the patient. The system determines a discrete list of electronic instruments 112 that will be assigned to all patients included in the logical registry 120 or sub-registry. For example, a shoulder sub-registry may select the Simple Shoulder Test (SST), American Shoulder Elbow Society (ASES), and a Single Assessment Numeric Evaluation (SANE) as the electronic instruments 112 to send. In this example, all selected electronic instruments 112 are released to all patients included in the particular sub-registry. The outcomes data from electronic instruments 112 can help determine the effectiveness of treatment, therapy, medication regimes, and other procedures for a particular patient. The outcomes data from electronic instruments 112 can assist in mapping the electronic instruments 112 to a profile object 105.

The registry management server 110 is also configured to collect implant data, e.g., by scanning a barcode included on an implant to send to the registry management server 110 information indicative of the implant and/or when the implant is being delivered. In an example, a registry board determines a list of implants to be included in the study. The registry board provides a contact at the implants company to assist the system in the creation of an implants data list (that promotes scanning of barcodes). The implants form will be generated in the system where the implants data will be entered along with any other operative information required for the registry.

Regarding patient satisfaction, the registry management server 110 uses its generated satisfaction form, a standardized form, such as CGCHAPS, and/or can generate specific questions for which answers are collected (e.g., from questions that are asked on most satisfaction forms)/For example, the question "how friendly was your physician" is asked on most satisfaction forms. When participants join the registry, they select what optional data and forms they will submit. Participants will be able to change their submission options.

The profile object 105 includes objective outcomes data 240. The objective outcomes data 240 can include references to EMR CCDA data described above. In addition, objective outcomes data 240 can include wearables data collected from a remote device 104, such as a heart rate monitor, pedometer, and so forth. Consent to collect wearable data from the remote device 104 can be automatically gathered using one or more wireless protocols, such as SMS messaging, as described below. Objective outcomes data 240 includes physician recorded feedback and outcomes data. The physician may rate a patient's compliance with therapy and may make a determination of the success of an operation or other procedure. This data can be compared to the outcomes data of a patient, such as that collected using the electronic instruments 112 to contextualize the outcomes data.

Patient education data 260 can be included in the profile object 105. Patient education data 260 includes data indicative of a patient's understanding of the operation and the expected results of that operation. For example, patient education data 260 can include what the patient has been told about the procedure itself, the recovery time of the procedure, the expected results of the procedure, whether the patient has been asked if they understand what a physician has told them, and so forth. In one example, patient data indicating higher patient education can be used to weight a patient's outcomes scores more heavily in the registry. In one example, patient data indicating a low patient education can trigger transmission of education data to the patient.

Patient billing data 270 can be a part of the profile object 105 data. Patient billing information can include a patient's outstanding balance, insurance information, past expenses, projected expenses, and so forth. The patient billing data 270 can be used to contextualize the outcomes data or other elements of the profile object 105 and can be used when mapping one or more electronic instruments 112 to a profile object 105.

The registry management server 110 performs data collection to populate a registry, e.g., based on patient consent. In an example, the registry management server 110 collects demographics information from an external system (e.g., a patient management system at a hospital) and/or from manual uploading and/or form receipt of medical history forms and EMRs. The consent of the patient can be obtained through a patient portal of the registries system using the client device 102 or the remote device 104. In some examples, the remote device 104 is a portable device or a wearable device. The data processing system can use a remote application to collect the data from the remote device 104. In some examples, a third party server, such as a server of a company that manufactured or designed the remote device 104, can collect the profile data from the remote device 104. Data, such as wearable data, collected from a wearable device of a patient or received from a third party server associated with the remote device 104 can be stored in the profile object 105.

To obtain patient consent to collect the wearable data from the remote device 104 or the third party server and store the data in the registry, a notification or alert can be sent to the wearable device or portable device as described above and presented to the patient on a user interface of the device or of another remote device 104. The request for consent to collect the remote device 104 data is sent using one or more protocols such as SMS messaging, a push notification, email, and so forth. Using the example of SMS messaging, the request for consent can be sent as a text message when the patient installs the application of the data processing system or at a later time. If other registries need to obtain consent, the registries management server sends the request wirelessly to the remote device 104 as needed. Such use of sending consent requests as needed can increase compliance and increase the data received by the registries management server for filling out profile objects 105 and registries. In turn, the robust profile data can result in a better mapping of electronic instruments 112 to patients for future procedures.

Figure 3:
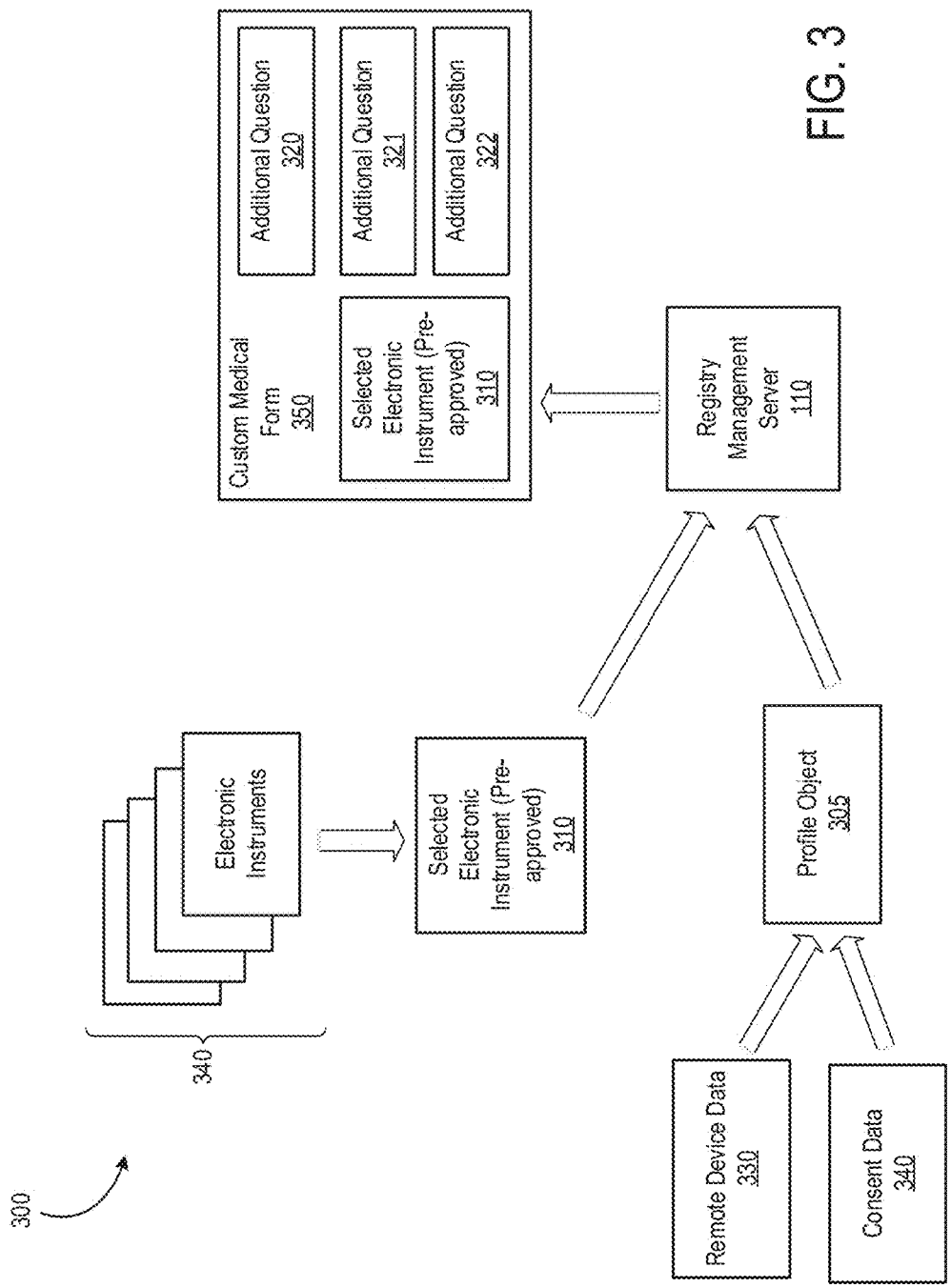
FIG. 3 is a flow diagram showing a custom electronic instrument.

FIG. 3 shows a block diagram 300 for creating a custom electronic instrument 350 using the profile object 105 data. A pre-approved or validated electronic instrument 310 is selected as being a potential electronic instrument for a patient in a registry. Remote device data 330 and consent data 340 is collected and added to the profile object 305 as described above. Other profile data in the profile object 305 can be sent to the registry management server 110 to determine if additional questions should be added to the validated electronic instrument. For example, if a patient is running every day after a total knee replacement and the activity is detected by a wearable device, a validated electronic instrument 310 can be appended with additional data to ask specific questions about the effects of the physical activity. A custom electronic instrument 350 can be created from the validated electronic instrument (which is approved for the registry) and additional questions (e.g., questions 320, 321, 322) so that the maximum amount of data can be added to the registry without having to re-approve the electronic instrument.

Figure 4:
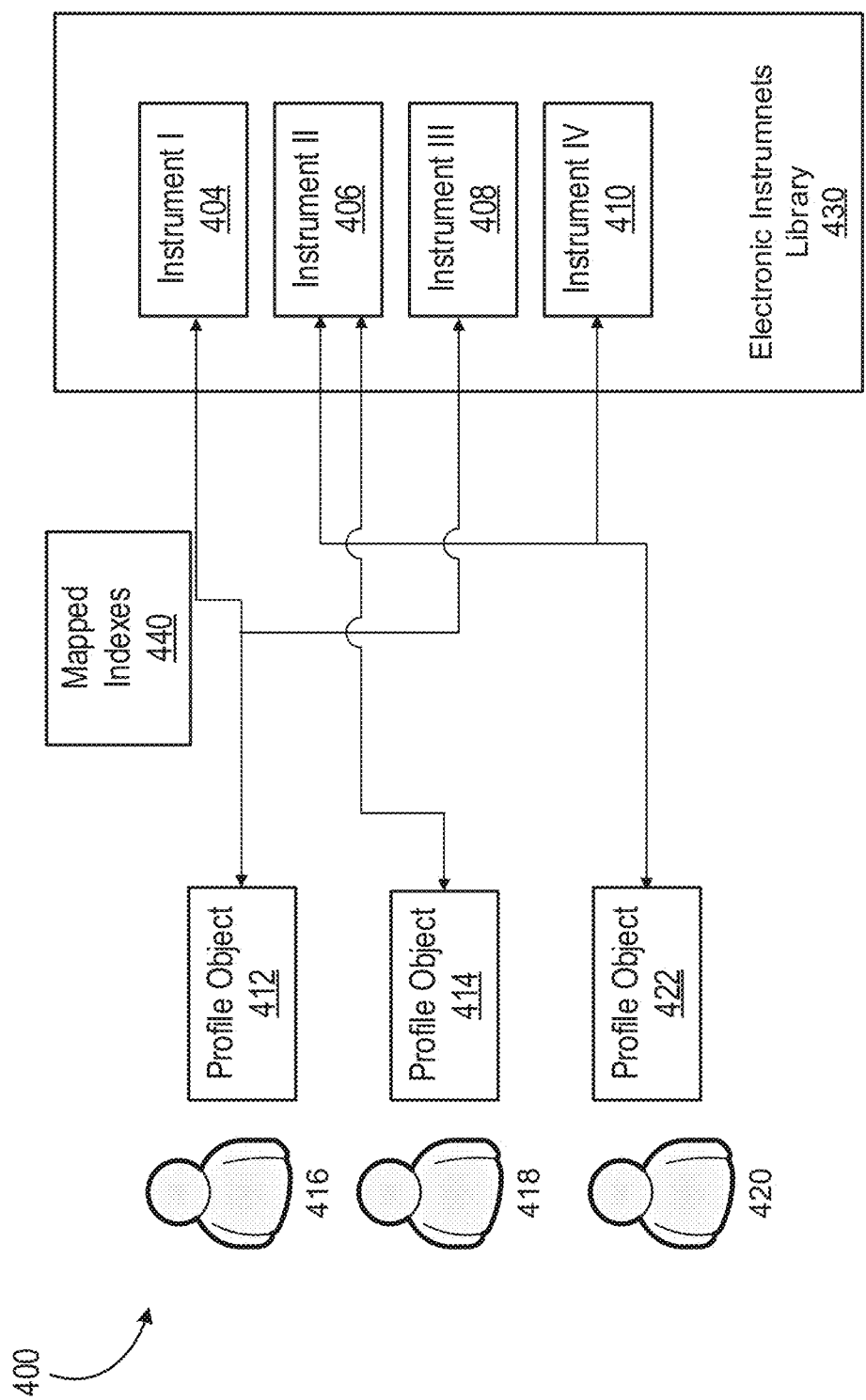
FIG. 4 is a diagram illustrating mapped references of profile objects.

FIG. 4 shows a diagram 400 of mapped indexes 107 between profile objects 412, 414, 422 and electronic instruments 404, 406, 408, and 410 of library 430. Mapped indexes 440 are added to the profile objects and are used to automatically enroll a patient of the profile objects 105 into one or more registries. The electronic instruments 112 can be generated as needed for profile objects 105. This avoids having to add the electronic instruments 112 data to the profile object 105 and allows for increased flexibility in managing the logical registries and sub-registries of the data processing system. One or more elements of the profile object 105 can be used to create the mapped indexes 440. A shared system is created with a common portal to manage all registries and sub-registries as needed. For example, the profile data can be used across the one or more registries as permitted for creating correlations data, statistical analysis, and so forth.

A logical table 60 is used to store the mapped indexes 107. The logical table 60 has logical rows and logical columns to form logical cells. Each logical row of the logical table 60 corresponds to one of the profile objects (e.g., profile objects 412, 414, and 422). The logical row for the profile object of a patient is configured to store the references of each electronic instrument of the electronic instruments library 430 to which the profile object is mapped. For example, the profile object 412 is mapped to instrument I 404 and instrument II 406. The logical row corresponding to profile object 412 includes references to both instrument I 404 and instrument II 406 rather than generating a copy of either electronic instrument itself into the profile object. To decrease search times and reduce lookup latency, the logical table 60 is indexed and the index for each profile object 105 is stored in the profile object 105. In this way, the electronic instruments mapped to the profile object can be quickly accessed, changed, deleted, updated, or otherwise manipulated by the registry management server as needed.

The logical table 60 is updated and expanded as the data processing system 100 determines that additional electronic instruments 112 are to be assigned to one or more profile objects and as more profile objects are added to the data repository 125. The logical table is dynamically assembled to minimize storage requirements. The logical table 60 thus acts as a bridge between the library 140 and the profile objects. New entries into the logical table 60 are indexed. This reduces latency for returning data indicating which electronic instruments have been assigned to a patient and can increase the speed in which registry analysis can occur. In addition, the flexibility of the data repository 125 is increased because manipulation of the associations between the profile objects and the library 140 can be achieved by updating the logical table 60 rather than updating each profile object 105.

Figure 5:
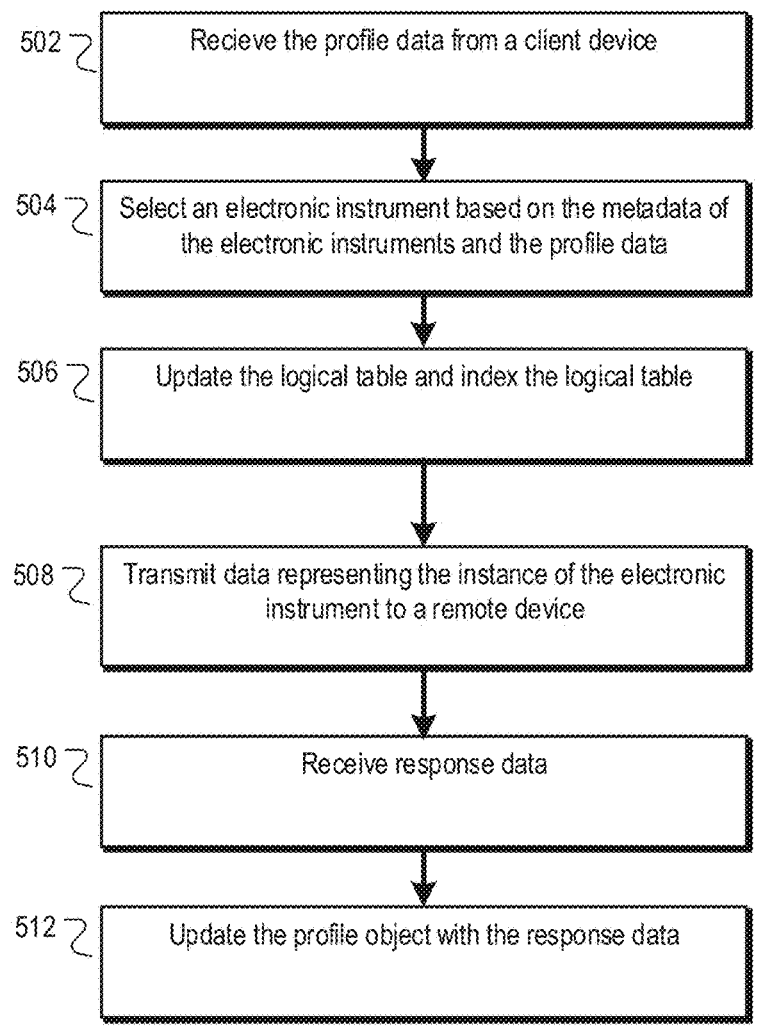
FIGS. 5-6 are flow diagrams showing processes for managing a logical registry.

FIG. 5 shows an example process 500 for collecting profile data using the electronic instrument by the registry management server 110. At block 502, profile data is received from a client or remote device 104. The patient can be simply registering with the system to create a profile object 105. The profile data can be entered from prior procedures or from the patient's medical history. At block 504 the profile object 105 data is used to select one or more electronic instruments 112 for the patient profile. If necessary, the patient is automatically enrolled in one or more registries. The mapped electronic instrument data is generated at block 506 for sending to the patient by updating the logical table 60. The electronic instrument is sent to a remote device 104 or client device 102 associated with the patient at block 508. The association can be made apparent in the profile object 105. At block 510, the registry management server 110 receives response data 115 from the remote device 104. At block 512, the profile object 105 of the patient is updated with the response data 115 for later use.

Figure 6:
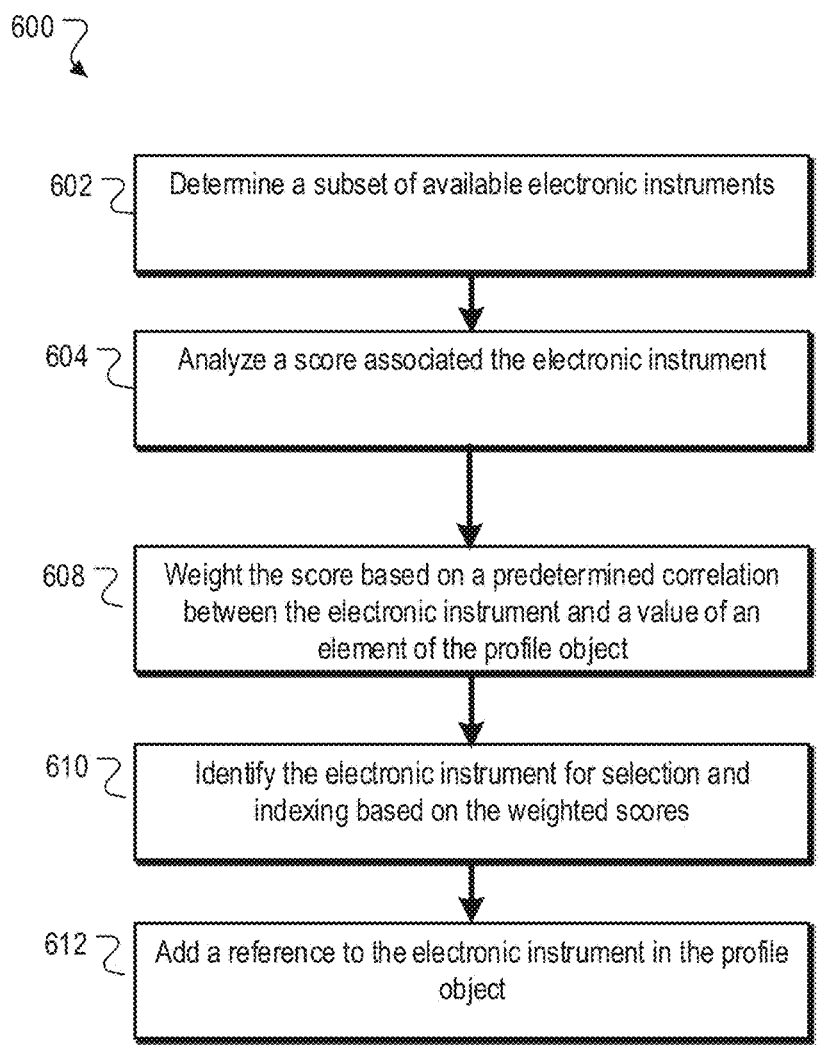

FIG. 6 shows a flow diagram 600 of an example procedure for selecting one or more electronic instruments 112 to a profile object 105. A subset of available electronic instruments 112 is found by the registry management server 110 at step 602 based on registry participation and profile data. Historical scores of the one or more electronic instruments 112 are analyzed at step 604. The score is weighted based on predetermined statistical correlations at block 608. The electronic instrument 112 is selected for mapping at step 610 based on the weighted score. At step 612, a reference to the selected electronic instrument 112 is added to the profile object 105.

Figure 7:
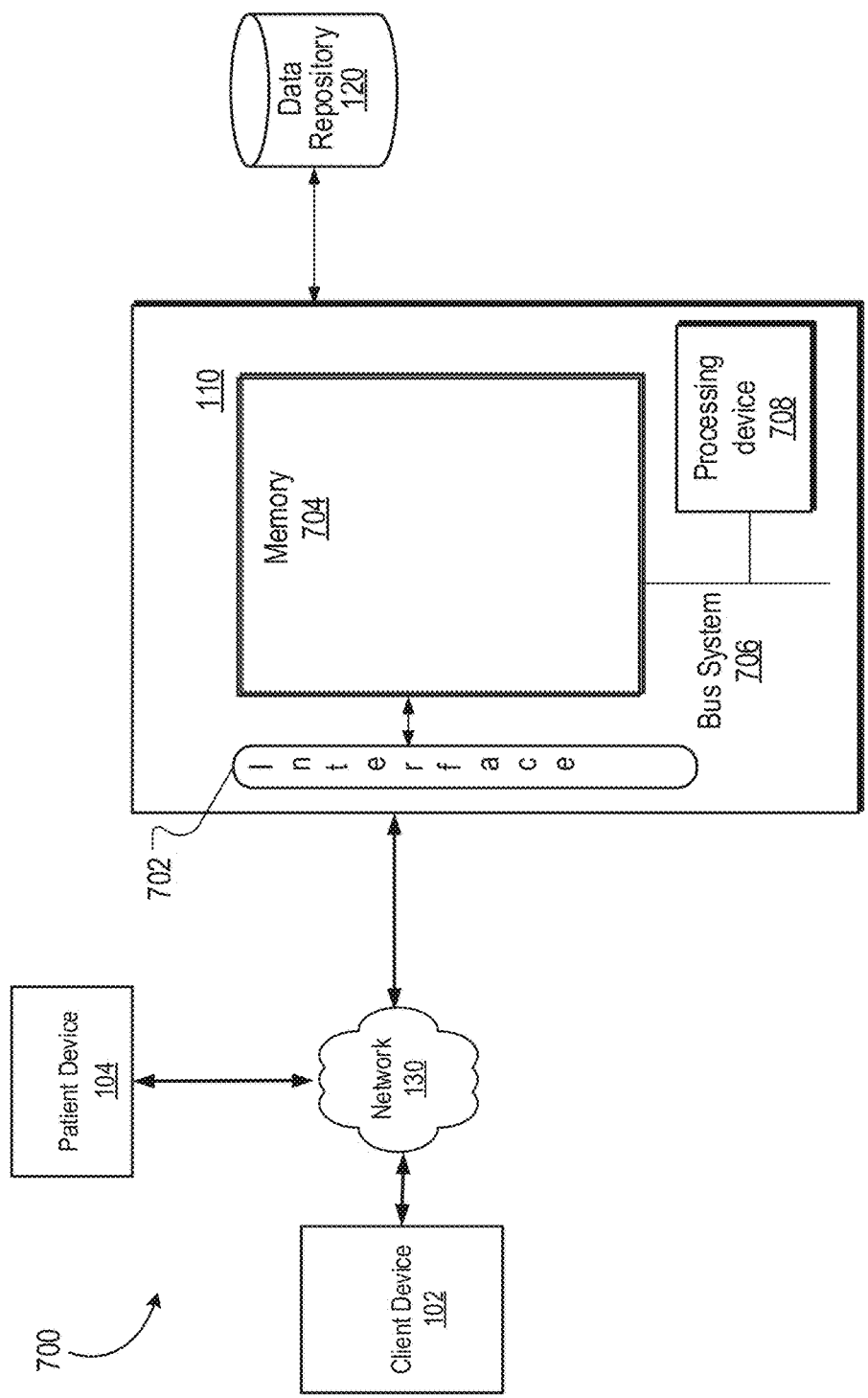
FIG. 7 is a block diagram showing an example of a registry management server 110.

FIG. 7 is a block diagram 700 of components of the data processing system. The client device 102 and the remote device 104 can be any sort of computing devices capable of taking input from a user and communicating over a network with the registry management server 110 and/or with other client or remote devices 104. Each of the client device 102 and the remote device 104 can be a mobile device, a desktop computer, a laptop, a cell phone, a personal digital assistant ("PDA"), a server, an embedded computing system, a mobile device and so forth.

The registry management server 110 can be any of a variety of computing devices capable of receiving information, such as a server, a distributed computing system, a desktop computer, a laptop, a cell phone, a rack-mounted server, and so forth. The registry management server 110 may be a single server or a group of servers that are at a same location or at different locations.

The registry management server 110 can receive information from one or more of the client device 102 and the remote device 104 via an interface 702. Interface 702 can be any type of interface capable of receiving information over a network, such as an Ethernet interface, a wireless networking interface, a fiber-optic networking interface, a modem, and so forth. The registry management server 110 also includes a processing device 708 and memory 704. A bus system 706, including, for example, a data bus and a motherboard, can be used to establish and to control data communication between the components of the registry management server 110. A processing device 708 may include one or more microprocessors. Generally, the processing device 708 may include any appropriate processor and/or logic (not shown) that is capable of receiving and storing data, and of communicating over a network 130. A memory 704 can include a hard drive and a random access memory storage device, such as a dynamic random access memory, machine-readable media, or other types of non-transitory machine-readable storage devices.

As used herein, the terms "computer" and "computer systems" refer broadly to any sort of combination of one or more servers and/or computing devices. As used herein, the terms "instrument(s)" and "electronic instrument(s)" refer broadly to any type of device and/or document (or any combination thereof), which presents data and/or information to a user and allows the user to input and/or send data and/or information to the system.

Embodiments can be implemented in digital electronic circuitry, in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web using browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the techniques described herein.

What is claimed is:

1. A data processing system for managing a logical registry, the data processing system comprising:
   a registry management server comprising one or more data processors; and
   one or more storage devices configured for communication with the registry management server, the one or more storage devices configured to store a logical registry comprising:
   a data repository comprising first profile data associated with a profile object, the data repository being configured to receive the first profile data from the registry management server;
   a library of electronic instruments each associated with metadata for use in mapping the electronic instruments and the profile object by the registry management server; and
   a logical table comprising a number of logical rows intersecting a number of logical columns to define a number of logical cells, a logical row of the number of logical rows corresponding to the profile object;
   the registry management server comprising one or more machine-readable hardware storage devices storing instructions that are executable by the one or more data processors to perform operations comprising:
   receiving second profile data from a client device, the second profile data associated with the profile object;
   selecting, based on the second profile data and the metadata, an electronic instrument from the library;
   mapping the electronic instrument and the profile object by performing operations comprising:
      updating the logical table by storing, in a logical cell of the number of logical cells, a reference to the selected electronic instrument, wherein the logical cell is in the logical row of the logical table corresponding to the profile object; and
      indexing the logical table;
   transmitting the selected instrument by:
      selecting data representing a question of the electronic instrument for transmission to a remote device based on a characteristic of received data from a portable remote device; and
      generating an alert from the selected data, with the alert comprising a universal resource locator (URL), which specifies a location of the registry management server for activating or viewing the selected data representing a question of the electronic instrument,
      wherein the alert activates a viewer application to cause the alert to display on the remote device and to enable connection via the URL to the registry management server over the Internet when the remote device is online;
   responsive to transmitting receiving response data from the remote device; and
   updating the profile object with the response data.

2. The data processing system of claim 1, the operations further comprising:
   generating electronic instrument data based on the selected electronic instrument;
   transmitting the electronic instrument data to a remote device;
   receiving, from remote device, response data associated with the electronic instrument data;
   updating the profile object with the response data; and
   responding to a query for data representing the profile object by returning the profile data, the response data, and the index of the logical row of the logical table corresponding to the profile object.

3. The data processing system of claim 1, wherein selecting the electronic instrument from the library comprises:
   determining a subset of electronic instruments from the library of electronic instruments that are available for selection based on a procedure of the patient;
   for each electronic instrument of the subset:
      analyzing a score associated the electronic instrument, the score being based on one or more performance ratings for the electronic instrument;
      weighting the score based on a predetermined correlation between the electronic instrument and a value of an element of the profile object;
      identifying the electronic instrument for selection based on the weighted score for each electronic instrument.

4. The data processing system of claim 3, wherein the element of the profile object comprises one of patient demographics data, patient clinical data, patient recorded outcomes data, objective outcomes data, patient satisfaction data, patient education data, and patient billing data.

5. The data processing system of claim 1, the operations further comprising:

automatically enrolling the patient in a sub-registry of the logical registry, the sub-registry being related to the electronic instrument and being for a particular type of procedure data, wherein access to the sub-registry is limited to patients who have submitted to the sub-registry the particular type of procedure data.

6. The data processing system of claim 1, the operations further comprising:

transmitting an SMS message to the remote device requesting consent to receive the portable remote device data;

receiving data representing the consent from the remote device; and requesting, from a third party server, the portable remote device data.

7. The data processing system of claim 1, the operations further comprising:

generating a custom electronic instrument comprising the electronic instrument and additional questions based on the mapping between the electronic instrument and the profile object.

8. The data processing system of claim 1, the operations further comprising:

generating a ranked list of a number of electronic instruments that are mapped to the profile object based on the profile data and the metadata; and transmitting, to the client device, data representing the ranked list.

9. A data processing system for managing a medical registry, the data processing system comprising:

a registry management server comprising one or more data processors; and one or more storage devices configured for communication with the registry management server, the one or more storage devices configured to store a medical registry comprising:

a data repository comprising patient data associated with a patient profile, the patient data being related to a medical treatment of a patient associated with the patient profile, the data repository being configured to receive the patient data from the registry management server;

a library of medical forms each associated with metadata for use in mapping the medical forms and the patient profile by the registry management server; and a logical table comprising a number of logical rows intersecting a number of logical columns to define a number of logical cells, a logical row of the number of logical rows corresponding to the patient profile;

the registry management server to configured perform operations comprising:

receiving second profile data from a client device, the second profile data associated with the patient profile;

selecting, based on the second profile data and the metadata, a medical form from the library;

mapping the selected medical form and the patient profile by performing operations comprising:

updating the logical table by storing, in a logical cell of the number of logical cells, a reference to the selected medical form, wherein the logical cell is in the logical row of the logical table corresponding to the patient profile; and indexing the logical table;

transmitting the selected medical form by:

selecting data representing a question of the selected medical form for transmission to a remote device based on a characteristic of received data from a portable remote device; and generating an alert from the selected data, with the alert comprising a universal resource locator (URL), which specifies a location of the registry management server for activating or viewing the selected data representing a question of the selected medical form, wherein the alert activates a viewer application to cause the alert to display on the remote device and to enable connection via the URL to the registry management server over the Internet when the remote device is online;

responsive to transmitting, receiving response data from the remote device; and updating the patient data with the response data.

10. A method comprising:

storing, using a data repository, a logical registry comprising:

a data repository comprising first profile data associated with a profile object, the data repository being configured to receive the first profile data from the registry management server;

a library of electronic instruments each associated with metadata for use in mapping the electronic instruments and the profile object by the registry management server; and a logical table comprising a number of logical rows intersecting a number of logical columns to define a number of logical cells, a logical row of the number of logical rows corresponding to the profile object;

receiving, using a registry management server, second profile data from a client device, the second profile data associated with the profile object;

selecting, using the registry management server, based on the second profile data and the metadata, an electronic instrument from the library; and mapping, using the registry management server, the electronic instrument and the profile object, wherein mapping comprises:

updating the logical table by storing, in a logical cell of the number of logical cells, a reference to the selected electronic instrument, wherein the logical cell is in the logical row of the logical table corresponding to the profile object;

indexing the logical table;

transmitting the selected instrument by:

selecting data representing a question of the electronic instrument for transmission to a remote device based on a characteristic of received data from a portable remote device; and generating an alert from selected data, with the alert comprising a universal resource locator (URL), which specifies a location of the registry management server for activating or viewing the selected data representing a question of the electronic instrument, wherein the alert activates a viewer application to cause the alert to display on the remote device and to enable connection via the URL to the registry management server over the Internet when the remote device is online;

responsive to transmitting, receiving response data from the remote device; and updating the profile object with the response data.

11. The method claim 10, further comprising:
generating electronic instrument data based on the selected electronic instrument;
transmitting the electronic instrument data to a remote device;
receiving, from remote device, response data associated with the electronic instrument data;
updating, the profile object with the response data; and
responding, to a query for data representing the profile object by returning, the profile data, the response data, and the index of the logical row of the logical table corresponding to the profile object.

12. The method claim 10, wherein selecting the electronic instrument from the library comprises:
determining a subset of electronic instruments from the library of electronic instruments that are available for selection based on a procedure of the patient;
for each electronic instrument of the subset:
analyzing a score associated the electronic instrument, the score being based on one or more performance ratings for the electronic instrument;
weighting the score based on a predetermined correlation between the electronic instrument and a value of an element of the profile object;
identifying the electronic instrument for selection based on the weighted score for each electronic instrument.

13. The method of claim 12, wherein the element of the profile object comprises one of patient demographics data, patient clinical data, patient recorded outcomes data, objective outcomes data, patient satisfaction data, patient education data, and patient billing data.

14. The method of claim 10, further comprising:
automatically enrolling the patient in a sub-registry of the logical registry, the sub-registry being related to the electronic instrument and being for a particular type of procedure data, wherein access to the sub-registry is limited to patients who have submitted to the sub-registry the particular type of procedure data.

15. The method of claim 10, further comprising:
transmitting an SMS message to the remote device requesting consent to receive the portable remote device data;
receiving data representing the consent from the remote device; and
requesting, from a third party server, the portable remote device data.

16. The method of claim 10, further comprising:
generating a custom electronic instrument comprising the electronic instrument and additional questions based on the mapping between the electronic instrument and the profile object.

17. The method of claim 10, further comprising:
generating a ranked list of a number of electronic instruments that are mapped to the profile object based on the profile data and the metadata; and
transmitting, to the client device, data representing the ranked list.

18. A non-transitory computer-readable medium storing instructions for performing operations comprising:
storing a logical registry comprising:
a data repository comprising first profile data associated with a profile object, the data repository being configured to receive the first profile data from the registry management server;
a library of electronic instruments each associated with metadata for use in mapping the electronic instruments and the profile object by the registry management server; and
a logical table comprising a number of logical rows intersecting a number of logical columns to define a number of logical cells, a logical row of the number of logical rows corresponding to the profile object;
receiving second profile data from a client device, the second profile data associated with the profile object;
selecting, based on the second profile data and the metadata, an electronic instrument from the library; and
mapping the electronic instrument and the profile object by performing operations comprising:
updating the logical table by storing, in a logical cell of the number of logical cells, a reference to the selected electronic instrument, wherein the logical cell is in the logical row of the logical table corresponding to the profile object; and
indexing the logical table;
transmitting the selected instrument by:
selecting data representing a question of the electronic instrument for transmission to the remote device based on a characteristic of received data from a portable remote device; and
generating an alert from selected data, with the alert comprising a universal resource locator (URL), which specifies a location of the registry management server for activating or viewing the selected data representing a question of the electronic instrument,
wherein the alert activates a viewer application to cause the alert to display on the remote device and to enable connection via the URL to the registry management server over the Internet when the remote device is online;
responsive to transmitting receiving response data from the remote device; and
updating the profile object with the response data.

19. The non-transitory computer-readable medium of claim 18, the operations further comprising:
generating electronic instrument data based on the selected electronic instrument;
transmitting the electronic instrument data to a remote device;
receiving, from remote device, response data associated with the electronic instrument data;
updating the profile object with the response data; and
responding to a query for data representing the profile object by returning the profile data, the response data, and the index of the logical row of the logical table corresponding to the profile object.

20. The non-transitory computer-readable medium of claim 18, wherein selecting the electronic instrument from the library comprises:
determining a subset of electronic instruments from the library of electronic instruments that are available for selection based on a procedure of the patient;
for each electronic instrument of the subset:
analyzing a score associated the electronic instrument, the score being based on one or more performance ratings for the electronic instrument;
weighting the score based on a predetermined correlation between the electronic instrument and a value of an element of the profile object;

identifying the electronic instrument for selection based on the weighted score for each electronic instrument.

21. The non-transitory computer-readable medium of claim 20, wherein the element of the profile object comprises one of patient demographics data, patient clinical data, patient recorded outcomes data, objective outcomes data, patient satisfaction data, patient education data, and patient billing data.

22. The non-transitory computer-readable medium of claim 18, the operations further comprising:

automatically enrolling the patient in a sub-registry of the logical registry, the sub-registry being related to the electronic instrument and being for a particular type of procedure data, wherein access to the sub-registry is limited to patients who have submitted to the sub-registry the particular type of procedure data.

23. The non-transitory computer-readable medium of claim 18, the operations further comprising:

transmitting an SMS message to the remote device requesting consent to receive the portable remote device data;

receiving data representing the consent from the remote device; and requesting, from a third party server, the portable remote device data.

24. The non-transitory computer-readable medium of claim 18, the operations further comprising:

generating a custom electronic instrument comprising the electronic instrument and additional questions based on the mapping between the electronic instrument and the profile object.

25. The non-transitory computer-readable medium of claim 18, the operations further comprising:

generating a ranked list of a number of electronic instruments that are mapped to the profile object based on the profile data and the metadata; and transmitting, to the client device, data representing the ranked list.

* * * * *